(12) United States Patent
Feit et al.

(10) Patent No.: US 10,916,139 B2
(45) Date of Patent: Feb. 9, 2021

(54) SYSTEM AND METHOD FOR POST-VEHICLE CRASH INTELLIGENCE

(71) Applicant: Beyond Lucid Technologies, Inc., Concord, CA (US)

(72) Inventors: Jonathon S. Feit, Pleasant Hill, CA (US); Christian Witt, Concord, CA (US)

(*) Notice: Subject to any disclaimer, the term of this patent is extended or adjusted under 35 U.S.C. 154(b) by 319 days.

(21) Appl. No.: 15/462,186

(22) Filed: Mar. 17, 2017

(65) Prior Publication Data

US 2017/0270252 A1 Sep. 21, 2017

Related U.S. Application Data

(60) Provisional application No. 62/310,093, filed on Mar. 18, 2016.

(51) Int. Cl.
| | | |
|---|---|---|
| *G16H 10/60* | (2018.01) | |
| *G08G 1/127* | (2006.01) | |
| *G08G 1/00* | (2006.01) | |
| *H04W 4/90* | (2018.01) | |

(52) U.S. Cl.
CPC ............ *G08G 1/127* (2013.01); *G08G 1/205* (2013.01); *G16H 10/60* (2018.01); *H04W 4/90* (2018.02)

(58) Field of Classification Search
CPC ........ G08G 1/127; G08G 1/205; G16H 10/60; H04W 4/90
See application file for complete search history.

(56) References Cited

U.S. PATENT DOCUMENTS

| | | | |
|---|---|---|---|
| 7,129,826 B2 | 10/2006 | Nitz et al. | |
| 7,152,785 B2 | 12/2006 | Metz et al. | |
| 8,482,534 B2 | 7/2013 | Pryor | |
| 8,482,535 B2 | 7/2013 | Pryor | |
| 9,659,484 B1 | 5/2017 | Mehta et al. | |
| 9,736,670 B2 | 8/2017 | Mehta et al. | |
| 9,756,169 B2 | 9/2017 | Mehta et al. | |
| 2002/0103622 A1* | 8/2002 | Burge | G07C 5/008 702/183 |
| 2006/0161315 A1 | 7/2006 | Lewis et al. | |
| 2012/0021386 A1* | 1/2012 | Anderson | G09B 9/052 434/66 |
| 2012/0094628 A1* | 4/2012 | Mader | H04W 4/90 455/404.1 |
| 2013/0072145 A1* | 3/2013 | Dantu | A61B 7/003 455/404.1 |
| 2014/0285216 A1 | 9/2014 | Cuddihy et al. | |
| 2016/0088455 A1 | 3/2016 | Bozik et al. | |
| 2017/0124853 A1 | 5/2017 | Mehta et al. | |
| 2017/0161614 A1 | 6/2017 | Mehta et al. | |
| 2017/0164175 A1 | 6/2017 | Bozik et al. | |
| 2017/0171735 A1 | 6/2017 | Anand et al. | |

(Continued)

FOREIGN PATENT DOCUMENTS

WO 2013033655 A1 3/2013

*Primary Examiner* — Reginald R Reyes
(74) *Attorney, Agent, or Firm* — DLA Piper LLP US

(57) ABSTRACT

A system and method to capture and aggregate occupant and incident information from within a vehicle following an accident, and to transmit such aggregated incident and patient data, in an automated and event triggered fashion, to an emergency responder. The data transmitted to the emergency responder can trigger creating a new patient record for the occupant of the vehicle.

31 Claims, 7 Drawing Sheets

(56) References Cited

U.S. PATENT DOCUMENTS

| | | |
|---|---|---|
| 2017/0180486 A1 | 6/2017 | Mehta et al. |
| 2017/0180964 A1 | 6/2017 | Mehta et al. |
| 2017/0195475 A1 | 7/2017 | Mehta et al. |
| 2017/0245130 A1 | 8/2017 | Mehta et al. |
| 2017/0251347 A1 | 8/2017 | Mehta et al. |

* cited by examiner

SYSTEM AND METHOD FOR POST-VEHICLE CRASH INTELLIGENCE

CROSS-REFERENCE OF RELATED APPLICATION

This application claims priority to and the benefit of U.S. Provisional Patent Application No. 62/310,093, filed on Mar. 18, 2016, the disclosure of which is incorporated herein by reference in its entirety.

FIELD OF THE DISCLOSURE

The present disclosure relates to medical transportation and public safety, which includes Fire, Emergency Medical Services/Prehospital Patient Care, Police, non-emergency medical transportation (also known as "Paratransit"), and more generally, transportation and logistics. Specifically, the present disclosure relates to post-crash information involving autonomous and so-called "smart" vehicles. This area of focus has, on occasion, been referred to as "post-crash intelligence."

BACKGROUND

Most innovations that are built into automobiles, boats, airplanes, busses, trains, and other vehicles today focus on keeping occupants (including both drivers and passengers) from getting involved in crashes in the first place (for example, RADAR, LIDAR, automatic breaking, lane controls, and more), or on reducing the force of an impact (for example, various types of automatic airbags, and other physical barriers such as crumple zones). Yet crashes still happen from time to time, and indeed, recent statistics show a drastic rise in the number of crashed within recent years, which has been attributed to distracted driving. Fire and/or emergency medical services may be needed when a crash happens, but little to no information about the occupants of the vehicle(s) involved in a crash is made available to emergency responders prior to their arrival at the crash site.

The current methods of dispatching emergency medical assistance to a vehicle crash include the following: (1) A "push" method, in which a summons for help is transmitted by satellite, radio, or cellular signal into a central dispatching station (a Public Safety Answering Point, or PSAP), where it triggers an assessment, response and intervention protocol. This trigger leads to either (a) the transmission of a signal to emergency responders via computer, hence the name of the computerized system (i.e., Computer-Aided Dispatch, or CAD), which is then received by a computerized module inside the emergency response vehicle or on the person of the emergency responders; or (b) the initiation of a human communication, usually by radio or cellular phone, to the emergency responders, that includes location and incident details. This is the method that is presently used by the popular vehicle-integrated emergency response system marketed under the "OnStar™" brand (and others like it): upon receipt of a crash-related or other emergency signal, the existing system contacts a PSAP directly—or a relay dispatch where an operator in turn contacts a PSAP—and initiates an emergency response. (2) A second "pull" or "self-initiated" method of emergency medical service dispatch, involves the direct observation of an emergency incident by a responder, who then "calls in" the emergency by directly contacting the PSAP and requesting the appropriate response resources.

SUMMARY

This present disclosure provides a technology, for example, a software system with several possible embodiments, including (1) one that is directly integrated into the vehicle; (2) one that is accessible remotely via a network ("cloud") server; (3) one that is contained on a device such as a mobile phone or a wearable computing device that is able to collect information about the vehicle either physically or virtually; and (4) one that is contained on a physical device such as a plug-in "dongle" that uses a port to connect to the vehicle (e.g., the onboard diagnostics port or another such connection point). All of these embodiments can collect, store, and as appropriate, securely share data about the vehicle and the occupants with emergency responders, either while the latter are en route to the scene if a network connection can be made and data transmitted wirelessly, or if no network access is available, then such information can be shared upon arrival at the vehicle through point-to-point communication methods including (but not limited to) Bluetooth, Wi-Fi, and Near-Field Communication. The software connects to a repository of critical medical details about the vehicle's occupants, with such data stored either in a local repository for secure access while offline (i.e., stored in or connected to the vehicle) or a virtual repository (i.e., a cloud-based storage facility).

In some embodiments, a method and a system for capturing, processing, and transmitting incident and patient information in a vehicle may comprise receiving signals from one or more vehicle sensors within the vehicle by a processor circuit connected to the vehicle, the signals indicating a vehicle crash. The processor circuit may initiate a communication to 9-1-1 and determine the vehicle's location. The processor circuit may receive biometric data related to an occupant of the vehicle from a biosensor. The processor circuit may retrieve personal and medical records of the occupant of the vehicle from a database and send the received biometric data and the retrieved personal and medical records to one or more emergency responding agencies.

In some embodiments, the processor circuit may be integrated in the vehicle by a vehicle manufacturer. In some embodiments, the processor circuit may be integrated in a plug-in computer which is connected to the vehicle through an on-board diagnostics II port. In some embodiments, the processor circuit may be integrated within a mobile device which is connected to the vehicle via a communication protocol, e.g., USB, Near-Field Communication, Bluetooth, Wi-Fi, etc.

In some embodiments, the vehicle sensors may comprise one or more of accelerometers, gyroscopes, crash sensors, seat belt sensors, and cameras. In some embodiments, the biometric data may comprise one or more of heart rate, blood pressure, blood type, blood alcohol level, blood sugar level, respiratory rate, pupillary movement, galvanic skin response, ability to focus eyes, ability to move, ability to speak, and state of consciousness.

In some embodiments, the processor circuit may transmit vehicle and occupant data directly to one or more emergency responders through a point-to-point communication method. In some embodiments, the point-to-point communication method may comprise Bluetooth, Wi-Fi, and Near-Field Communication.

In some embodiments, in response to the data sent by the processor circuit, one or more new patient records may be created for the occupant or occupants of the vehicle within a software system that is used by the one or more emergency responding agencies.

DETAILED DESCRIPTION

Figure 1:
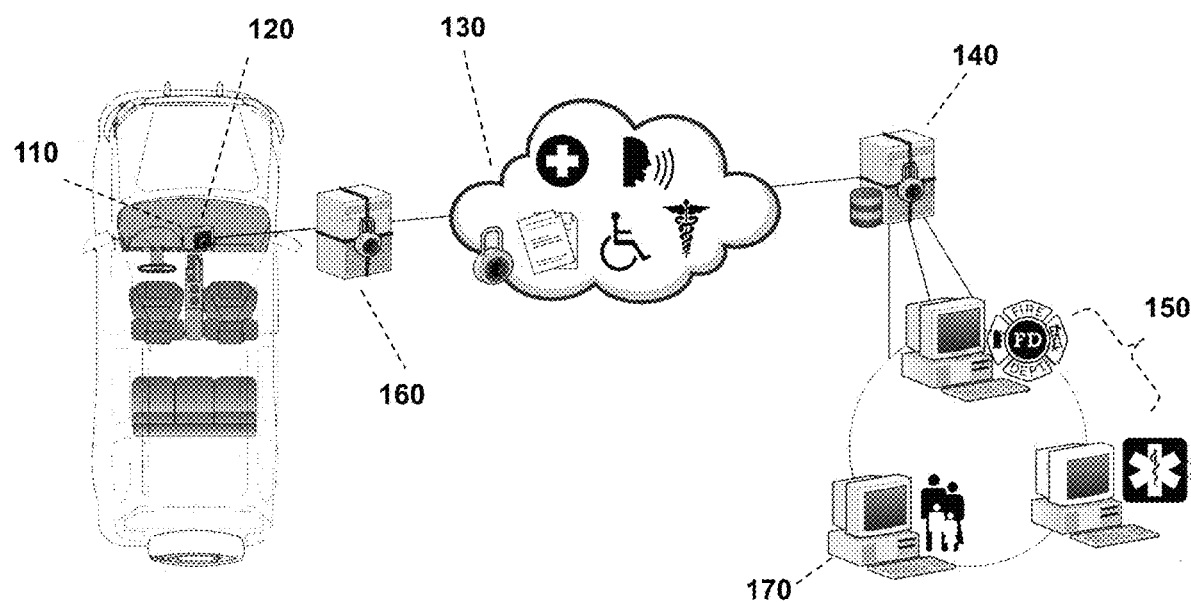
FIG. 1 is a diagram of a post-crash intelligence system according to some embodiments of the present disclosure.

The moments between when a motor vehicle accident (MVA) occurs and when emergency medical services or the fire department arrive on the scene to help are critical, as they can mean the difference between life and death. The advent of flame retardant chemicals dropped the incidence of fires by 75-85% during the latter half of the 20th century. Comparable innovations in vehicles now confer a previously unimaginable level of safety. However, by and large, the innovations that have been built into vehicles such as automobile, airplanes, boats, busses, trains, and trucks, have focused on keeping operators and passengers from getting involved in an accident in the first place, or reducing the force of an impact when possible. Yet crashes happen from time to time, and when they do, emergency medical services may be needed to rescue operators and passengers, sometimes by extricating and/or resuscitating them to save their lives. Due to a lack of meaningful information originating at the accident scene and transmitted directly to the responding department, most emergency medical service agencies head to the scene upon notice from an vehicle operator, a passenger, a bystander, and/or an integrated communications system such as OnStar™, as if they are prepared for the worst possible scenario. For example, a patient who is experiencing a life-or-death medical crisis coupled with a vehicle on fire. An agency's highest level of preparedness assumes that the patient will be unable to offer meaningful details about the incident or the individuals involved.

The present disclosure relates to a software system that is integrated into the vehicle itself to serve as a local repository of critical medical information about the driver and/or passengers. When a vehicle crash occurs for which emergency response is needed (e.g., above a certain speed threshold, from an angle that statistically or algorithmically correlates with severe bodily harm, or in which an airbag deploys, etc.), the software will use vehicle location information (provided by GPS, cell tower triangulation, or other localization methods) to determine the vehicle's position and contact the most appropriate emergency response agency, based either on a database that is integrated within the software, or a network-accessible list of regional emergency resources.

The described system serves an emerging field of transportation and logistics engineering known as "post-crash intelligence." It relates to a system and method for alerting emergency medical responders not only as to the location of a vehicle (for example, passenger car, truck, bus, airplane, train, snowmobiles, skiing, hiking, biking motorcycle, snowmobile, maritime vessel, or other similar land, sea, or air), that has been involved in a collision or some other accident, but also of the identity of the driver and likely passengers, their health status in general, and their current medical status. The present disclosure presents a combination of location, vehicular, and medical information, transmitted securely over a network to an emergency response documentation system and computer aided dispatch program. Existing systems in this field—some of which are commercially well known, such as the integrated vehicular communications system commonly called OnStar™—address only the status and location of the vehicle, but not its occupants.

The present disclosure shows a system and method of notifying emergency responders about the condition of a vehicle's occupants after a crash or other emergency incident. It can utilize signals generated by the vehicle's crash computer and/or other sensors built into the vehicle, or a summons for assistance generated by an occupant of the vehicle, which triggers a call for assistance that either (a) contacts the PSAP and notifies the appropriate fire and/or emergency medical response agency based on the vehicle's vicinity, while sending certain information about the vehicle and its occupants directly to the agency as the crew is en route to the incident scene (having been dispatched by the PSAP); or (b) in certain locations, where a PSAP cannot be contacted, the system directly notifies the appropriate fire and/or emergency medical service agency about the condition of the vehicle (including its location), as well as the condition of its occupants. The information received by the emergency medical response crew auto-populates an electronic patient care record (ePCR) software application that is currently used and accessible by emergency responders while they are at their station and/or in the field already en route to the incident scene. The system connects to emergency response agencies via an "over the air" network, such as cellular network in order to send data to the emergency response unit prior to its arrival at the crash scene. In some embodiments, the system may send data by connecting to a portable satellite communication system, or a mobile radio base station which may be known as a "cell on wheels" (COW) or a "tower on wheels" (TOW). In the absence of an "over-the-air" network, emergency responders that arrive on-scene can use one or more of the following: Near-Field Communication (NFC), Bluetooth, and similar point-to-point communication methods to populate data from a software application that is contained within the vehicle; stored on a mobile phone or other portable device that is carried or worn an occupant of the vehicle; or connected to the vehicle either physically, e.g., via the on-board diagnostics II (OBD-II) port, or virtually, e.g., via one or more of the aforementioned point-to-point communication means.

One embodiment of this disclosure combines vehicular sensors and medical sensors, and a patient care documentation program residing on a computer within the vehicle or connected to the computer virtually via a secure network, out of view of the passengers but "always on." In some embodiments, the vehicular sensors may comprise accelerometers, gyroscopes; crash computers; cameras that are contained within or connected to the vehicle; integrated sensors in the seat, seat belt, steering wheel, mirrors, etc.; and even ambient sensors for cabin temperature, humidity, etc. In some embodiments, medical sensors may comprise any combination of blood pressure monitor, heart rate monitor, wearables sensor, galvanic skin response sensor, blood alcohol or glucose level monitor, and monitors to detect wakefulness and mental status, among other vital conditions. The computer is capable of connecting to a data receiving portal and dispatch system in-use by regional emergency responders.

FIG. 1 is an example of a vehicle in which software that is capable of providing event-triggered and/or on-demand notifications, and that transmits information about the vehicle's occupant(s) (i.e., its operator(s) and/or passenger(s)), including their identities and physical conditions before and after the incident the triggered an emergency response, and/or the condition, location, and movement of the vehicle. In some embodiments the system needs not provide both occupant data and vehicle data, but may provide only occupant data. The system runs on an integrated computer with an embedded operating system 110 that is connected to the vehicle through an interface 120 either directly (i.e., stored on an integrated onboard computer, or using an OBD II port attachment) or virtually (i.e., connected via NFC, Bluetooth, Wi-Fi, or other network data exchange channel). For security purposes, limited occupant health information are stored locally on the vehicle's computer. A majority of data 160 is stored on a secure device (e.g., cell phone) or on a remotely accessible computer server using one of a variety of methods for attaining an encrypted network connection 130 including but not limited to NFC, Bluetooth, Wi-Fi, Long-Term Evolution (LTE). Database 140 stores information about the registered vehicle owner and any frequent passengers' personal identifiable information, photo, and limited medical history of the sort that emergency responders need to know in order to intervene effectively. Database 140 can be connected to a dispatch-and-charting software 150 that is used by the responding agency. In some embodiments, database 140 can also be connected to a software program 170 used by non-EMS authorized parties that are affiliated with the occupants of the vehicle e.g., family members, healthcare providers, legal guardians, insurance providers, employers, etc.

Figure 2:
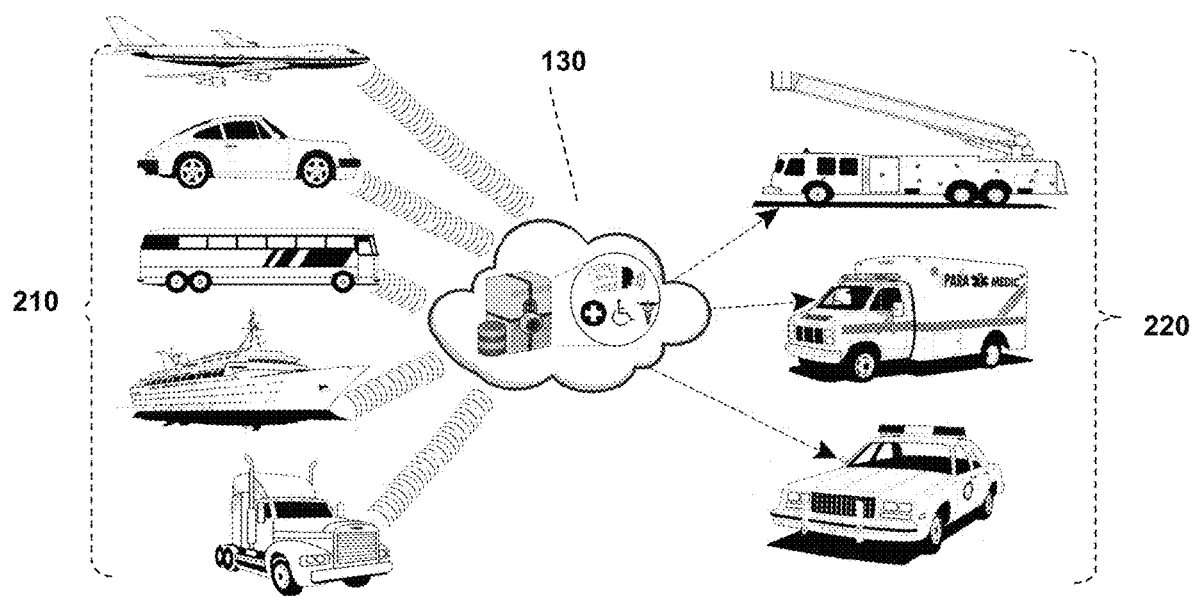
FIG. 2 shows the flow of vehicle and occupant information according to some embodiments of the present disclosure.

FIG. 2 is a schematic demonstrating the flow of information from several types of vehicles 210 (including, but not limited to, automobiles, airplanes, maritime vessels, busses, trains, and trucks) in which software is operated as described in FIG. 1. In some embodiments, the system can transmit information about the vehicle's one or more occupants to a data receiving portal and dispatch system in-use by emergency responders via an encrypted secure network 130. Emergency responders 220 who are dispatched and en route to the incident scene including firefighters, paramedics, police, officers, can receive the occupant data via secure network.

Figure 3:
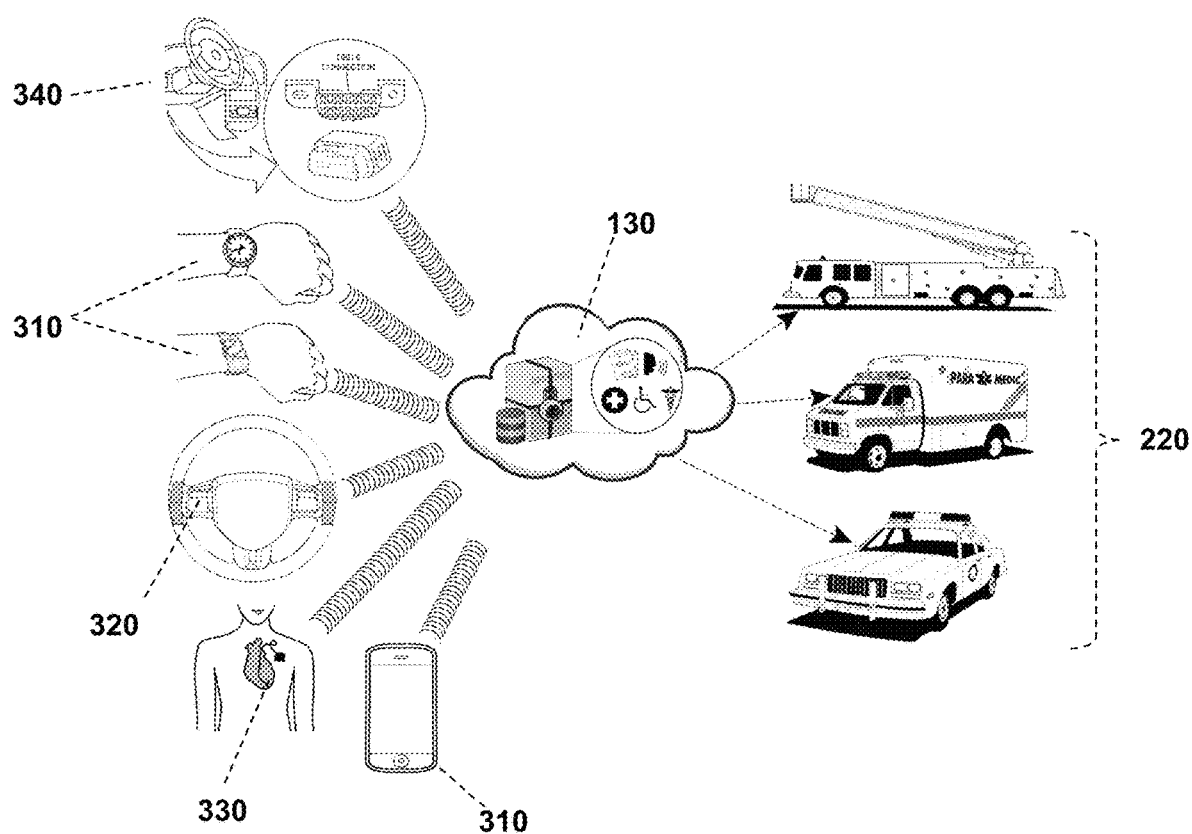
FIG. 3 shows methods by which data is obtained in vehicles according to some embodiments of the present disclosure.

FIG. 3 is a schematic demonstrating several methods by which data originating in the vehicle, including from sensors on or in the person of the operator(s) and/or passenger(s), or on or in the structure or software of the vehicle itself (including, but not limited to, embedded sensors and sensors that connect to the vehicle's computer via communications protocol such as Bluetooth, wired, wireless network or cellular connection, are transmitted securely beyond the walls of the vehicle by way of software as described in FIG. 1, using a server that transmits the data to the appropriate emergency response agency. In some embodiments, the sensors can be those integrated in an occupant's mobile devices 310 including but not limited to a mobile phone, a wearable device, etc. For example, the sensors may measure user's body temperature, heart rate, skin response, blood alcohol or glucose level. In some embodiments, the sensors can be sensors 320 which are integrated in the vehicle including but not limited to monitors which can detect occupants' wakefulness and mental status. In some embodiments, the sensors can be monitors 330 which may monitor status of an implantable medical device and transmit data wirelessly. In some embodiments, the sensors can be vehicle sensors 340. The vehicle sensors 340 can be sensors integrated in the vehicle by a vehicle manufacturer. The vehicle sensors 340 can also be sensors that are plugged in and connected to the vehicle through an interface e.g., an OBD-II interface, etc. The vehicle sensors 340 may provide vehicle related information such as direction and force of an impact, number of occupants in the vehicle, locations of occupants in the vehicle, occupants' bodyweights, and torque and movement of occupants' bodies. In some embodiments, signals from the sensors can be sent to the responding agency via an encrypted secure network 130. The emergency responders who are dispatched and en route to the incident scene may receive corresponding data from the agency via a secure network 130. In some embodiments, a secure network may not be available for computer 110 to send data or for emergency responders to receive data. When the emergency responders arrive at the scene, they can communicate directly with computer 110 to obtain related information through an interface including but not limited to USB, Wi-Fi, Bluetooth, NFC, etc.

Figure 4:
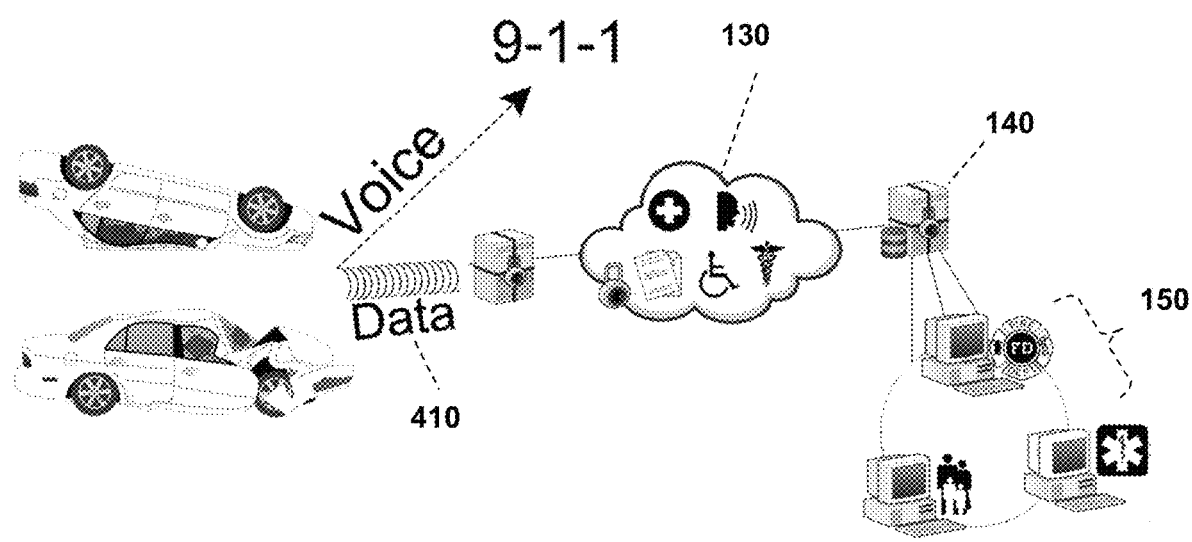
FIG. 4 shows how the data is transmitted to an emergency response agency according to some embodiments of the present disclosure.

FIG. 4 is a schematic demonstrating the use of the software described in FIG. 1 to transmit data 410 (including, but not limited to, health details, advanced directives, disability accommodations, linguistic requirements and restrictions, known health conditions including allergies, provider impressions and chief complaint, vehicle registration and insurance, next-of-kin emergency contact list, and list of authorized drivers) to the emergency response agency as demonstrated in FIG. 3, while voice communications to a public safety answering point offers human support while waiting for emergency responders to arrive. Also shown in FIG. 4. is the ability of the embedded software to send triggered, real-time notifications and updates about the vehicle operator(s) and/or passenger(s) to pre-authorized non-emergency personnel, in accordance with applicable laws and regulations. FIG. 4 also illustrates a structure of a patient care documentation system, including secure server and applications for data collection, aggregation, documentation, analysis, and transmission among the various parties that have a stake in a patient's care, including emergency responders; non-emergency caregivers including (but not limited to) doctors, nurses, community paramedics, skilled care facilities, and paratransit agencies; and family members, legal guardians or other parties who have been duly authorized to access a patient's information following a vehicular incident requiring emergency response. In some embodiments, database 140 with patient care information can be connected to a dispatch-and-charting software 150 that is used by the responding agency. In some embodiments, vehicle-related information can be gathered and sent to the emergency responders. The vehicle-related information may comprise insurance, registration, authorized drivers, a list of frequent vehicle operators and/or passengers. In some embodiments, personal health records may comprise advanced health directives, next-of-kin contact information, and lists of allergies, current medications, past surgeries, transplant registry status, and pre-existing conditions, including (if applicable) the presence of an implantable medical device that can transmit data wirelessly to emergency medical responders upon or prior to arrival, accessibility needs, and preferred form of communication, i.e., spoken language and need for translators.

Figure 5:
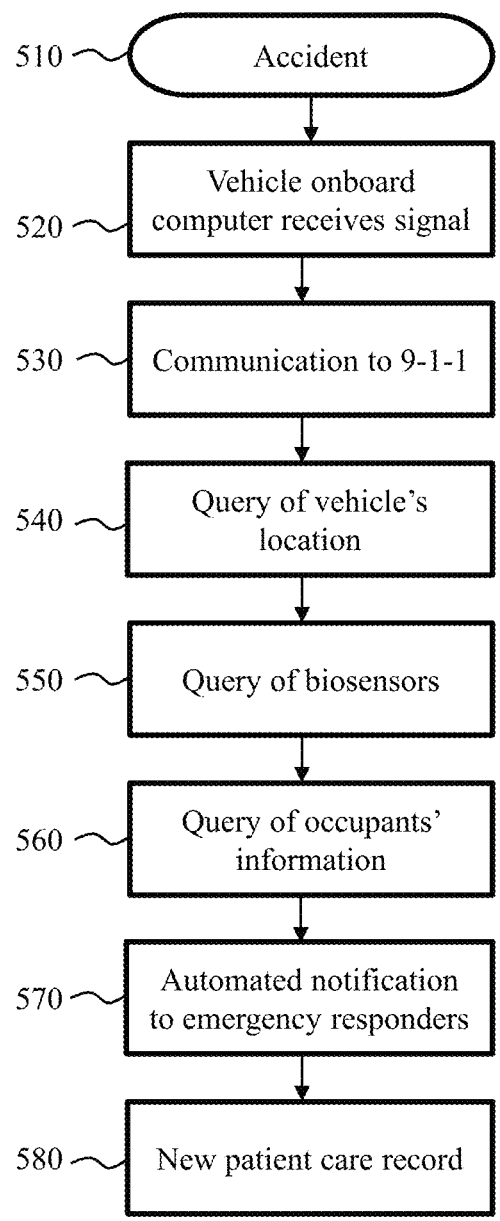
FIG. 5 is a flow diagram of a method of collecting and transmitting patient-occupant information according to some embodiments of the present disclosure.

FIG. 5 shows a flow diagram of a method for triggering the collection and transmission of incident and patient-occupant data from a motor vehicle following a crash or other emergency incident according to some embodiments of the present disclosure.

At step 510, an incidence of a crash, collision, rollover, or other impact occurs in which the vehicle is damaged or subjected to high external forces, such as might cause an airbag to deploy.

At step 520, a vehicle onboard computer, and possibly in conjunction with (but not reliant upon) an external device that contains an accelerometer, detect a collision of sufficient force that an emergency medical response to care for the vehicle's occupants may be warranted. In some embodiments, this vehicle onboard computer can be a computer or a control unit which vehicle manufacturers install on the vehicle. In some embodiments, this vehicle onboard computer can be an aftermarket add-on computer which is integrated with the vehicle's information systems and control systems. In some embodiments, the onboard computer may receive signals from one or more accelerometers in the vehicle which measure an excessive acceleration indicating the vehicle may be damaged or subjected to high external forces. In some embodiments, the onboard computer may receive signals from one or more airbag sensors in the vehicle which indicate airbags are deployed. In some embodiments, the vehicle onboard computer may receive signals from any combination of accelerometers, gyroscopes, airbag sensors, or other sensors such as cameras that are contained within or connected to the vehicle, integrated sensors in the seat, seat belt, steering wheel, mirrors, etc., and ambient sensors for cabin temperature, etc.

At step 530, once the vehicle onboard computer detects a collision of sufficient force that an emergency medical response may be needed, it may initiate a communication (e.g., phone call, text message, multi-media message, email, etc.) to 9-1-1 (or the appropriate emergency medical response phone number) using a modem, cellular hotspot, or similar telecommunications device contained within, or physically or virtually linked to the vehicle. In some embodiments, the vehicle onboard computer may coordinate with other devices such as one or more mobile devices present in the vehicle to initiate a communication to 9-1-1. For example, the vehicle onboard computer may send a notification or request to the one or more mobile devices which instructs the one or more mobile devices to initial a communication to 9-1-1.

At step 540, the vehicle onboard computer may make a query of the vehicle's location, using GPS or another location-awareness mechanism, by the dispatch-and-charting software package that resides on a computer in the vehicle or that is attached to it. GPS location may be generated by a sensor that is contained within the vehicle, or linked to it physically or virtually (as described above), or by querying a sensor within a mobile phone or wearable device that is carried or worn by an occupant of the vehicle, and is linked to the vehicle either physically or virtually.

At step 550, the vehicle onboard computer may make a query of biosensors that are built into the vehicle and/or any wearable biosensors (such as heart rate monitors, pedometers, pulse oximeters, etc.) that are carried by one or more of the vehicle occupants, provide a range of biometric data about the vehicle's occupant(s). These data are aggregated and broadcast securely, then imported by the dispatch-and-charting software running on the computer contained within the vehicle and/or on a device that is linked to the vehicle. Data that can be adapted from such biosensors include, but are not limited to, (1) the number of occupants in the vehicle at the time of the emergency incident, (2) each occupant's weight, (3) the elapsed time since each occupant's body moved, and (4) each occupant's several vital signs (such as heart rate, blood pressure, respiratory rate, pupillary movement and ability to focus eyes, galvanic skin response, and other bio-information).

At step 560, the vehicle onboard computer may make a query of a database that includes the registered vehicle owner and any frequent passengers' personal identifiable information, photo, and limited medical history of the sort that emergency responders need to know in order to intervene effectively on behalf of vehicle occupant(s) who are experiencing medical distress. For example, the health database may contain—but is not limited to—information about whether the owner of the vehicle and/or one or more frequent passengers is diabetic; has certain allergies; is prone to stroke or heart attack; has a history of seizure; has an implanted medical device; has a chronic disease or disability; has a communicable disease, or other relevant health information. Such personal and health-related information is compiled by the dispatch-and-charting software, then combined with data about or imported from the vehicle, including (but not limited to): (1) vehicle type, (2) seat positions for each occupant; (3) each occupant's weight (if available via an integrated sensor in the seat); (3) personal and health-related information and a photo of the vehicle's registered owner and/or any frequent passengers that have registered into a subscriber database so emergency responders can quickly identify them upon arrival at the scene; and (4) data about the incident itself, i.e., crash location, velocity and angle of impact; and whether a cabin penetration, rollover or airbag deployment occurred.

At step 570, the vehicle onboard computer may send an automated event-triggered notification to the fire or emergency medical services unit that has been or will be dispatched to the incident scene, based on geolocation and a query of a nationwide database of emergency responders that is contained within the dispatch-and-charting software and/or is accessible via the internet (if network access is possible). A responding agency selection algorithm includes, among other criteria, location awareness, a directory of emergency medical response agencies by location and type (i.e., fire vs. medical), and the nature of the emergency response (e.g., vehicle extraction, fire, medical, etc.), based on inputs received by the dispatch-and-charting software application as it compiles data as described in previous steps.

At step 580, receipt of the event-triggered notification by the responding emergency medical services unit triggers the creation of a new patient care record in the dispatch-and-charting software that is used by the responding agency, as long as that agency's dispatch-and-charting software meets certain minimum technical requirements. As long as such technical requirements are satisfied, the data captured may be automatically submitted to the responder's software program. The data received via software application may be proprietary, but it is compliant with at least one published, industry-recognized data standard such as: the National EMS Information System (NEMSIS), the Continuity of Care Document (CCD), the Consolidated-Clinical Document Architecture (C-CDA), the National Fire Incident Report System (NFIRS), the Criminal Justice Information Services (CJIS), and/or systems used by state motor vehicle, organ transplant and medical device implant registries. In some embodiments, the data may be compliant with other broadly accepted clinical documentation standards that may emerge.

Figure 6:
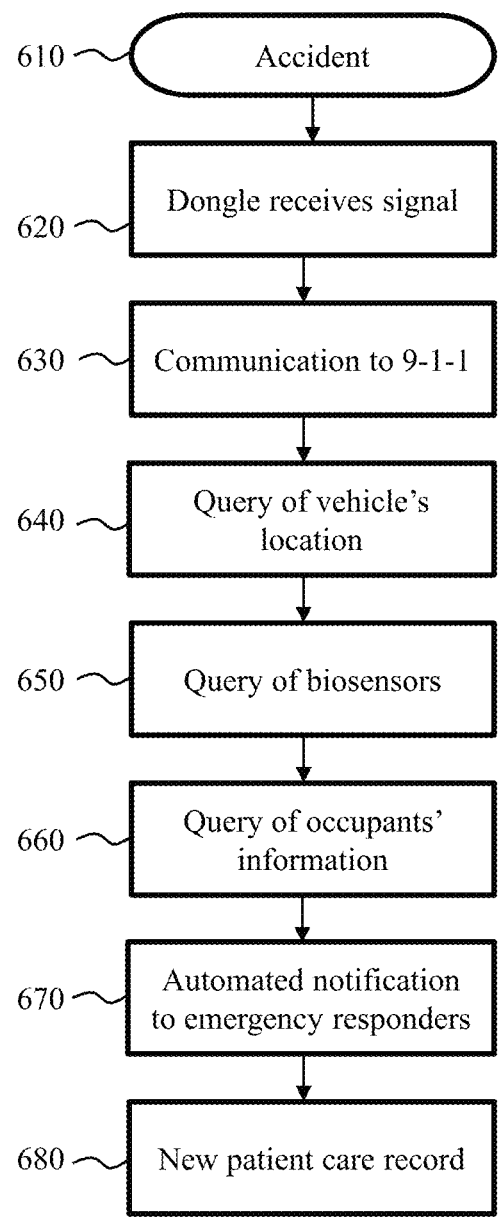
FIG. 6 is a flow diagram of a method of collecting and transmitting patient-occupant information according to some embodiments of the present disclosure.

FIG. 6 shows a flow diagram of another method for triggering the collection and transmission of incident and patient-occupant data from a motor vehicle following a crash or other emergency incident according to some embodiments of the present disclosure. In some embodiments, instead of using a vehicle onboard computer, a dongle computer can be connected to the vehicle through an interface which includes, but not limited to an OBD-II interface. As shown in step 620, the dongle computer can receive signals from vehicle sensors including but not limited to accelerometers, airbag sensors, and seat belt sensors, through this interface. Once the dongle detects a collision of sufficient force that an emergency medical response is needed, it may initiate a call to 9-1-1 at step 630, make a query of the vehicle's location at step 640, make a query of biosensors at step 650, make a query of occupants' information at step 660. It may send an automated notification to emergency responders at step 670. In some embodiments, a new patent care record may be created at step 680.

Figure 7:
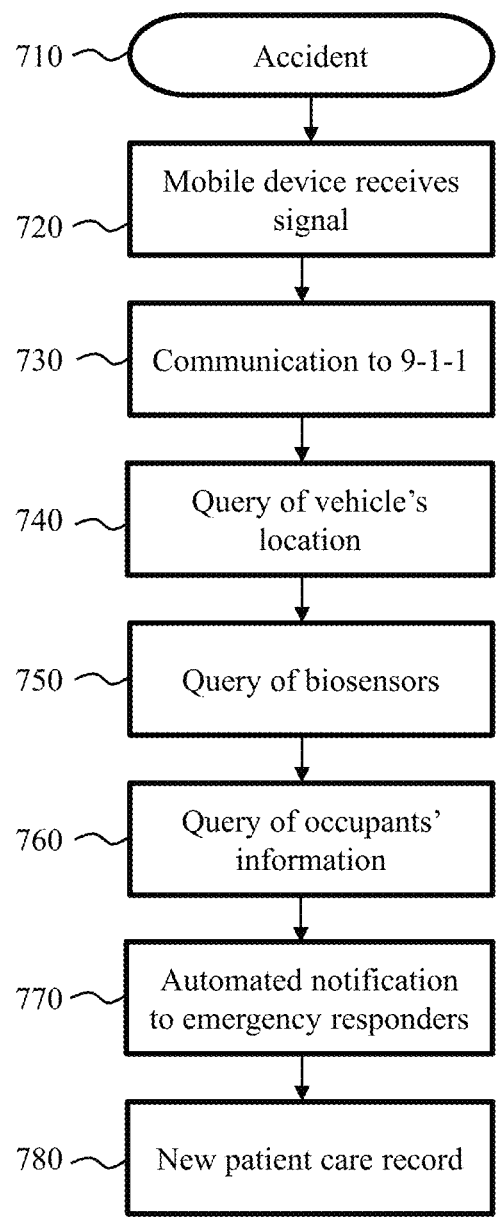
FIG. 7 is a flow diagram of a method of collecting and transmitting patient-occupant information according to some embodiments of the present disclosure.

FIG. 7 shows a flow diagram of another method for triggering the collection and transmission of incident and patient-occupant data from a motor vehicle following a crash or other emergency incident according to some embodiments of the present disclosure. In some embodiments, instead of using a vehicle onboard computer or a dongle computer, one or more mobile devices may be used. The one or more mobile devices can connect to the vehicle's control system and receive signals from vehicle sensors through one or more interfaces including but not limited to NFC, Bluetooth, Wi-Fi, USB. As shown in step 720, the one or more mobile devices can receive signals from vehicle sensors including but not limited to accelerometers, gyroscopes, airbag sensors, and seat belt sensors, through this interface. Once the one or more mobile devices detect a collision of sufficient force that an emergency medical response is needed, they may initiate a call to 9-1-1 at step 730, make a query of the vehicle's location at step 740, make a query of biosensors at step 750, make a query of occupants' information at step 760. They may send an automated notification to emergency responders at step 770. A new patent care record may be created at step 780.

The present disclosure is not to be limited in scope by the specific embodiments described herein. Indeed, other various embodiments of and modification to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes.

What is claimed is:

1. A method for capturing, processing, and transmitting incident and patient information in a vehicle, comprising:

receiving, by a processor circuit connected to the vehicle, signals from one or more vehicle sensors within the vehicle indicating a vehicle accident;

initiating, by the processor circuit, a communication to 9-1-1;

determining, by the processor circuit, the vehicle's location;

receiving, by the processor circuit, biometric data from a biosensor, the biometric data related to an occupant of the vehicle;

obtaining, from a secure storage of a phone or wearable device in local communication with the vehicle, personal and medical records of a registered user of the phone or wearable device;

establishing, by the processor circuit, a wireless connection with at least one computing device of one or more emergency responding agencies through a local network, the wireless connection being separate from the initiated communication to 9-1-1; and sending, by the processor circuit, the received biometric data and the retrieved personal and medical records to the one or more emergency responding agencies through the established wireless connection.

2. The method of claim 1, wherein the processor circuit is integrated in the vehicle by a vehicle manufacturer.

3. The method of claim 1, wherein the processor circuit is integrated in a plug-in computer which is connected to the vehicle.

4. The method of claim 3, wherein the plug-in computer is connected to the vehicle through an on-board diagnostics II port.

5. The method of claim 1, wherein the processor circuit is integrated within a mobile device, the mobile device being connected to the vehicle via a communication protocol.

6. The method of claim 5, wherein the communication protocol comprises one or more of USB, Near-Field Communication, Bluetooth, and Wi-Fi.

7. The method of claim 1, wherein the one or more vehicle sensors comprise one or more of accelerometers, gyroscopes, crash sensors, seat belt sensors, and cameras.

8. The method of claim 1, wherein the biometric data comprises one or more of heart rate, blood pressure, blood type, blood alcohol level, blood sugar level, respiratory rate, pupillary movement, galvanic skin response, ability to focus eyes, ability to move, ability to speak, and state of consciousness.

9. The method of claim 1, wherein the local network comprises at least one of Bluetooth, Wi-Fi, and Near-Field Communication.

10. The method of claim 1, comprising triggering a creation of a new patient record for the occupant of the vehicle within a software system used by the one or more emergency responding agencies.

11. The method of claim 1, further comprising identifying, by the processor circuit, the one or more emergency responding agencies prior to the sending, the identifying including selecting the one or more emergency responding agencies from a directory of emergency medical response agencies based on the vehicle's location.

12. The method of claim 1, wherein the determining is performed using GPS or another location-awareness mechanism.

13. The method of claim 1, wherein the personal and medical records of the occupant of the vehicle comprise information enabling identification of the occupant of the vehicle at the location of the vehicle.

14. The method of claim 1, wherein the sending comprises formatting the received biometric data and the retrieved personal and medical records according to an emergency medical services (EMS) industry data standard.

15. The method of claim 14, wherein the data standard is one of a National EMS Information System (NEMSIS), a Continuity of Care Document (CCD), a Consolidated-Clinical Document Architecture (C-CDA), a National Fire Incident Report System (NFIRS), or a Criminal Justice Information Services (CJIS).

16. A system for capturing, processing, and transmitting incident and patient information in a vehicle, comprising:
one or more vehicle sensors;
one or more biosensors;
a processor circuit coupled to the one or more vehicle sensors and the one or more biosensors, and configured to execute instructions causing the processor circuit to:
receive signals from one or more vehicle sensors within the vehicle indicating a vehicle accident;
initiate a communication to 9-1-1;
determine the vehicle's location;
receive biometric data from the one or more biosensors, the biometric data related to an occupant of the vehicle;
obtain, from a secure storage of a phone or wearable device in local communication with the vehicle, personal and medical records of a registered user of the phone or wearable device;
establish a wireless connection with at least one computing device of one or more emergency responding agencies through a local network, the wireless connection being separate from the initiated communication to 9-1-1; and
send the received biometric data and the retrieved personal and medical records to the one or more emergency responding agencies through the established wireless connection.

17. The system of claim 16, wherein the processor circuit is integrated in the vehicle by a vehicle manufacturer.

18. The system of claim 16, wherein the processor circuit is integrated in a plug-in computer which is connected to the vehicle.

19. The system of claim 18, wherein the plug-in computer is connected to the vehicle through an on-board diagnostics II port.

20. The system of claim 16, wherein the processor circuit is integrated within a mobile device, the mobile device being connected to the vehicle via a communication protocol.

21. The system of claim 20, wherein the communication protocol comprises one or more of USB, Near-Field Communication, Bluetooth, and Wi-Fi.

22. The system of claim 16, wherein the one or more vehicle sensors comprise one or more of accelerometers, gyroscopes, crash sensors, seat belt sensors, and cameras.

23. The system of claim 16, wherein the biometric data comprises one or more of heart rate, blood pressure, blood type, blood alcohol level, blood sugar level, respiratory rate, pupillary movement, galvanic skin response, ability to focus eyes, ability to move, ability to speak, and state of consciousness.

24. The system of claim 16, wherein the local network comprises at least one of Bluetooth, Wi-Fi, and Near-Field Communication.

25. The method of claim 11, the identifying further comprising determining an accident type based on the signals from the one or more vehicle sensors, wherein the selecting is further based on the accident type.

26. The system of claim 16, wherein the instructions further cause the processor circuit to identify the one or more emergency responding agencies prior to the sending by selecting the one or more emergency responding agencies from a directory of emergency medical response agencies based on the vehicle's location.

27. The system of claim 26, wherein the instructions further cause the processor circuit to determine an accident type based on the signals from the one or more vehicle sensors, wherein the selecting is further based on the accident type.

28. The system of claim 26, wherein the processor circuit is configured to determine the vehicle's location using GPS or another location-awareness mechanism.

29. The system of claim 16, wherein the personal and medical records of the occupant of the vehicle comprise information enabling identification of the occupant of the vehicle at the location of the vehicle.

30. The system of claim 16, wherein the sending comprises formatting the received biometric data and the retrieved personal and medical records according to an emergency medical services (EMS) industry data standard.

31. The system of claim 30, wherein the data standard is one of a National EMS Information System (NEMSIS), a Continuity of Care Document (CCD), a Consolidated-Clinical Document Architecture (C-CDA), a National Fire Incident Report System (NFIRS), or a Criminal Justice Information Services (CJIS).

* * * * *